(12) United States Patent  
Randle

(10) Patent No.: US 11,007,025 B2  
(45) Date of Patent: May 18, 2021

(54) ROBOT TOOL RETRACTION

(71) Applicant: CMR Surgical Limited, Cambridge (GB)

(72) Inventor: Steven James Randle, Cambridge (GB)

(73) Assignee: CMR SURGICAL LIMITED, Cambridge (GB)

(*) Notice: Subject to any disclaimer, the term of this patent is extended or adjusted under 35 U.S.C. 154(b) by 409 days.

(21) Appl. No.: 15/545,454

(22) PCT Filed: Jan. 21, 2016

(86) PCT No.: PCT/GB2016/050125  
§ 371 (c)(1),  
(2) Date: Jul. 21, 2017

(87) PCT Pub. No.: WO2016/116753  
PCT Pub. Date: Jul. 28, 2016

(65) Prior Publication Data  
US 2018/0008359 A1  Jan. 11, 2018

(30) Foreign Application Priority Data

Jan. 21, 2015 (GB) ..................................... 1501031

(51) Int. Cl.  
*A61B 34/32* (2016.01)  
*A61B 34/30* (2016.01)  
*A61B 34/00* (2016.01)

(52) U.S. Cl.  
CPC .............. *A61B 34/32* (2016.02); *A61B 34/30* (2016.02); *A61B 34/70* (2016.02); *A61B 2034/301* (2016.02); *A61B 2034/302* (2016.02)

(58) Field of Classification Search  
CPC ... A61B 34/32; A61B 34/70; A61B 2034/301; A61B 2034/302; A61B 34/30  
See application file for complete search history.

(56) References Cited

U.S. PATENT DOCUMENTS 5,086,401 A * 2/1992 Glassman .............. B25J 9/1679  
700/259  
5,184,601 A * 2/1993 Putman .................... A61B 1/00  
128/4

(Continued)

FOREIGN PATENT DOCUMENTS

EP 1 815 950 A1 8/2007  
WO 2013116869 A1 8/2013

OTHER PUBLICATIONS

United Kingdom Search Report for Application No. GB1501031.7, dated Jun. 15, 2015, 4 pages.

(Continued)

*Primary Examiner* — Jeff A Burke  
*Assistant Examiner* — Kyle T Johnson  
(74) *Attorney, Agent, or Firm* — Finch & Maloney PLLC

(57) ABSTRACT

A robot comprising: a base; a flexible arm extending from the base having: a plurality of joints positioned throughout the arm, a plurality of drivers arranged to drive the joints, and an attachment structure for attaching a tool to the arm; and a control unit configured to control the drivers and to receive inputs from sensors, where the control unit (i) controls the drivers to permit the arm to be reconfigured by the action of an external force applied to the arm to cause the tool to be retracted from a port; and (ii) on receiving sensor input indicating that the arm has been reconfigured to cause the tool to be retracted from the port, controls the drivers to reconfigure the arm so as to agitate the tool transverse to a longitudinal axis of the tool.

20 Claims, 3 Drawing Sheets

(56) References Cited

U.S. PATENT DOCUMENTS

| | | | |
|---|---|---|---|
| 6,233,504 B1* | 5/2001 | Das | B25J 9/1689 |
| | | | 414/4 |
| 6,436,107 B1* | 8/2002 | Wang | A61B 1/00149 |
| | | | 318/568.11 |
| 6,788,018 B1* | 9/2004 | Blumenkranz | B25J 9/0018 |
| | | | 128/DIG. 7 |
| 9,943,964 B2 | 4/2018 | Hares | |
| 2002/0120252 A1* | 8/2002 | Brock | A61B 17/00 |
| | | | 606/1 |
| 2002/0120254 A1* | 8/2002 | Julian | A61B 34/35 |
| | | | 606/1 |
| 2003/0055410 A1* | 3/2003 | Evans | A61B 34/32 |
| | | | 606/1 |
| 2003/0097060 A1* | 5/2003 | Yanof | A61B 34/70 |
| | | | 600/424 |
| 2005/0096502 A1* | 5/2005 | Khalili | A61B 1/313 |
| | | | 600/106 |
| 2006/0293643 A1 | 12/2006 | Wallace et al. | |
| 2006/0293646 A1* | 12/2006 | Whayne | A61B 18/148 |
| | | | 606/27 |
| 2007/0013336 A1 | 1/2007 | Nowlin et al. | |
| 2007/0138992 A1* | 6/2007 | Prisco | A61B 34/37 |
| | | | 318/568.21 |
| 2011/0040305 A1* | 2/2011 | Gomez | B25J 9/1661 |
| | | | 606/130 |
| 2011/0130718 A1* | 6/2011 | Kidd | A61B 34/30 |
| | | | 604/95.01 |
| 2013/0116706 A1 | 5/2013 | Lee et al. | |
| 2014/0142592 A1* | 5/2014 | Moon | A61B 34/37 |
| | | | 606/130 |
| 2014/0195052 A1* | 7/2014 | Tsusaka | A61B 34/76 |
| | | | 700/257 |
| 2014/0200851 A1* | 7/2014 | Weir | A61B 34/30 |
| | | | 702/182 |
| 2014/0228862 A1* | 8/2014 | Inoue | A61B 34/37 |
| | | | 606/130 |
| 2015/0282828 A1* | 10/2015 | Kishi | A61B 17/2909 |
| | | | 600/106 |
| 2015/0351857 A1 | 12/2015 | Vander Poorten et al. | |
| 2016/0184032 A1 | 6/2016 | Romo et al. | |
| 2016/0228203 A1* | 8/2016 | Yamanaka | A61B 1/05 |
| 2017/0367774 A1 | 12/2017 | Scholan | |
| 2018/0008359 A1 | 1/2018 | Randle | |

OTHER PUBLICATIONS

PCT Search Report & Written Opinion for Application No. PCT/GB2016/050125, dated May 10, 2016, 9 pages.

* cited by examiner

ROBOT TOOL RETRACTION

RELATED APPLICATIONS

This application claims priority under 35 U.S.C. § 371 as a national stage application of PCT Application No. PCT/GB2016/050125, filed Jan. 21, 2016, which claims priority to GB 1501031.7, filed Jan. 21, 2015, each of which is hereby incorporated herein by reference in its entirety.

This invention relates to a robot and control of that robot's movement of an attached tool.

BACKGROUND

FIG. 1 illustrates a surgical robot 1 in the course of performing an invasive medical procedure on a patient 9. The robot comprises an arm 2 which is articulated by means of multiple flexible joints 3 along its length. At the distal end 4 of the arm is a surgical tool. The surgical tool has a thin elongate shaft 5 with a device 6 at its distal end for engaging in the medical procedure. The device could, for example, be a cutting, grasping or imaging device. The surgical tool is attached to the arm via a wrist joint 3a of the arm. The wrist joint is configurable to adjust the direction in which the shaft 5 extends whilst the majority of the arm 2 remains static. The surgical tool is inserted into the patient's body through a surgical port 7.

During the procedure, an incision is made through the skin of the patient, and the port manually pushed into place. The port comprises a hollow tube 8 which passes through the outer tissues of the patient. This helps to limit disruption to those tissues as tools are inserted and removed, and as the robot manipulates the tools within the patient's body. The port retains its position via static friction with the surrounding skin and tissues. During a typical robotic laparoscopic surgery, tools are inserted and withdrawn through the port 7 many times, for example to enable the tools to be cleaned or swapped for different tools. When retracting the tool from the body through the port, force may be exerted on the port which pulls it loose. This may happen, for example, as a result of the static friction between the tool shaft 5 and the port as the tool is extracted, which may be significantly higher than when the clean tool was inserted through the port due to the tool shaft's interaction with the surgical site. In another example, this may happen as a result of the tool getting caught in the port, for example the device at the distal end of the tool may get caught in the port. If the port pulls out of the body, this can cause tearing and damage of the skin and tissues surrounding the incision. Bleeding is likely. Additionally, such an event can cause disruption to the ongoing medical procedure and damage to the surgical site inside the body, particularly if there are still some instruments inside the body which passed through the affected port.

In a manual laparoscopic surgery, this problem is generally avoided by the surgeon manually holding the port in place during extraction of a tool. It is known in robotic laparoscopic surgery to secure the port to the robot arm so that the port does not pull loose on extraction of the tool. This solution significantly constrains the movement of the arm and hence the tool. It also means that a port is only able to be used by a particular robot arm, so in a procedure which uses multiple robot arms, they would need to access the surgical site via different ports.

There is thus a need for a less restrictive solution to preventing a port from becoming loose when extracting a tool through the port during robotic laparoscopic surgery.

SUMMARY OF INVENTION

According to a first aspect there is provided a robot comprising: a base; a flexible arm extending from the base and having: a plurality of joints whereby the configuration of the arm can be altered, a plurality of drivers arranged to drive the joints to move, and an attachment structure for attaching a tool to the arm; and a control unit configured to control the drivers and operable in a retraction mode in which, whilst a tool is attached to the attachment structure and captive in a port, it: (i) controls the drivers to reconfigure the arm so as to cause the tool to be retracted from the port along a longitudinal axis of the tool; and (ii) on retracting the tool from the port along a longitudinal axis of the tool, controls the drivers to reconfigure the arm so as to agitate the tool transverse to the longitudinal axis of the tool.

The control unit may be configured to control the drivers to agitate the tool by causing the attachment structure to rotate about the longitudinal axis of the tool.

The control unit may be configured to control the drivers to agitate the tool by causing the angular attitude of the attachment structure relative to the base to be varied.

The control unit may be configured to control the drivers to agitate the tool transverse to the longitudinal axis of the tool as a function of the retraction along the longitudinal axis of the tool.

The robot may further comprise a tool attached to the attachment structure, the tool being a surgical tool.

The control unit may be configured to: receive inputs from sensors, and on receiving sensor input indicating that the arm has been reconfigured so as to cause the tool to be retracted from the port along a longitudinal axis of the tool, control the drivers to reconfigure the arm so as to agitate the tool transverse to the longitudinal axis of the tool.

The arm may comprise a plurality of sensors for sensing forces applied about the joints, and the control unit may be configured to, in the retraction mode, control the drivers in dependence on the outputs of the sensors.

The tool may comprise a plurality of sensors for sensing forces applied to the tool, and the control unit may be configured to, in the retraction mode, control the drivers in dependence on the output of the sensors.

The control unit may be configured to control the drivers to permit the arm to be reconfigured by the action of an external force applied to the arm so as to cause the tool to be retracted from the port along the longitudinal axis of the tool.

In the retraction mode, the control unit may be configured to control the drivers to prevent the arm from being reconfigured by the action of an external force applied to the arm so as to cause the tool to move transverse to the longitudinal axis of the tool.

In the retraction mode, the control unit is configured to control the drivers to prevent the arm from being reconfigured by the action of an external force applied to the arm so as to cause the tool to be further inserted into the port along a longitudinal axis of the tool.

The control unit may be configured to, in the retraction mode, control the drivers so as to resist the action of gravity and thereby cause the arm to maintain a configuration imposed by the external force independently of the action of gravity.

The control unit may be configured to, in the retraction mode, control the drivers so as to present a limited resistance to reconfiguration under the external force independently of the action of gravity.

The control unit may be configured to initiate operation in the retraction mode in response to receiving input from the operator via a user control interface.

The control unit may be configured to control the drivers to reconfigure the arm so as to cause the tool to be retracted from the port along a longitudinal axis of the tool in response to receiving a control input from the operator via the user control interface.

The control unit may be operable in a driven mode in which, when a tool is attached to the attachment structure, it receives a demand signal indicating a desired location of a part of the tool, calculates a configuration of the arm in which the part of the tool will be at the desired location and the tool intersects the location of the port, and controls the drivers so the arm adopts the calculated configuration.

The control unit may comprise a processor and a memory storing non-transiently a set of instructions executable by the processor for implementing the mode.

The robot may be a surgical robot.

According to a second aspect there is provided a method for controlling a robot, the robot comprising a base, a flexible arm extending from the base and having a plurality of joints whereby the configuration of the arm can be altered, a plurality of drivers arranged to drive the joints to move, and an attachment structure for attaching a tool to the arm, the method comprising, whilst a tool is attached to the attachment structure and captive in a port: controlling the drivers so as to reconfigure the arm so as to cause the tool to be retracted from the port along a longitudinal axis of the tool; and on retracting the tool from the port along a longitudinal axis of the tool, controlling the drivers to reconfigure the arm so as to agitate the tool transverse to the longitudinal axis of the tool.

BRIEF DESCRIPTION OF THE DRAWINGS

The invention will be described by way of example with reference to the accompanying figures. In the figures.

DETAILED DESCRIPTION

A surgical robot may have an arm and a tool attached to the arm. The arm may have a series of flexible joints which allow the arm to be reconfigured and also allow the position and direction of the tool to be altered. The robot may be able to sense the configuration of its joints. For a surgical procedure, a port can be sited in a patient. The tool enters the patient through the port. On sensing that the tool is being removed from the patient through the port, the arm can be reconfigured so as to agitate the tool transverse to the longitudinal axis of the tool, for example by twisting the tool about the longitudinal axis of the tool. Static friction between the tool and the port is thereby reduced, reducing the likelihood of the port becoming loose on removal of the tool.

Figure 1:
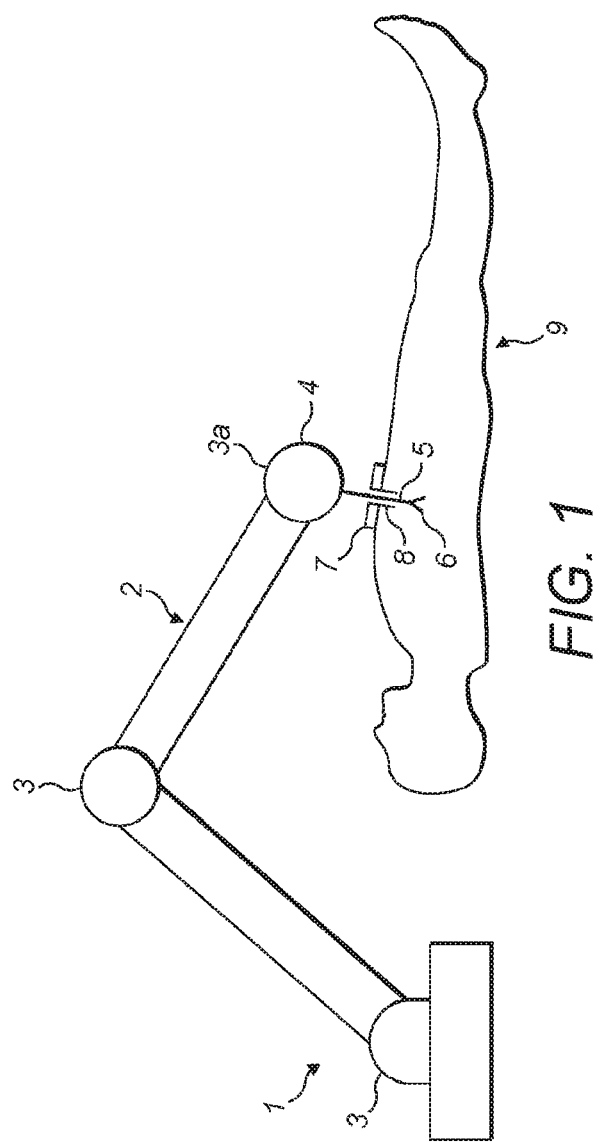
FIG. 1 illustrates a surgical robot performing a surgical procedure.
Figure 2:
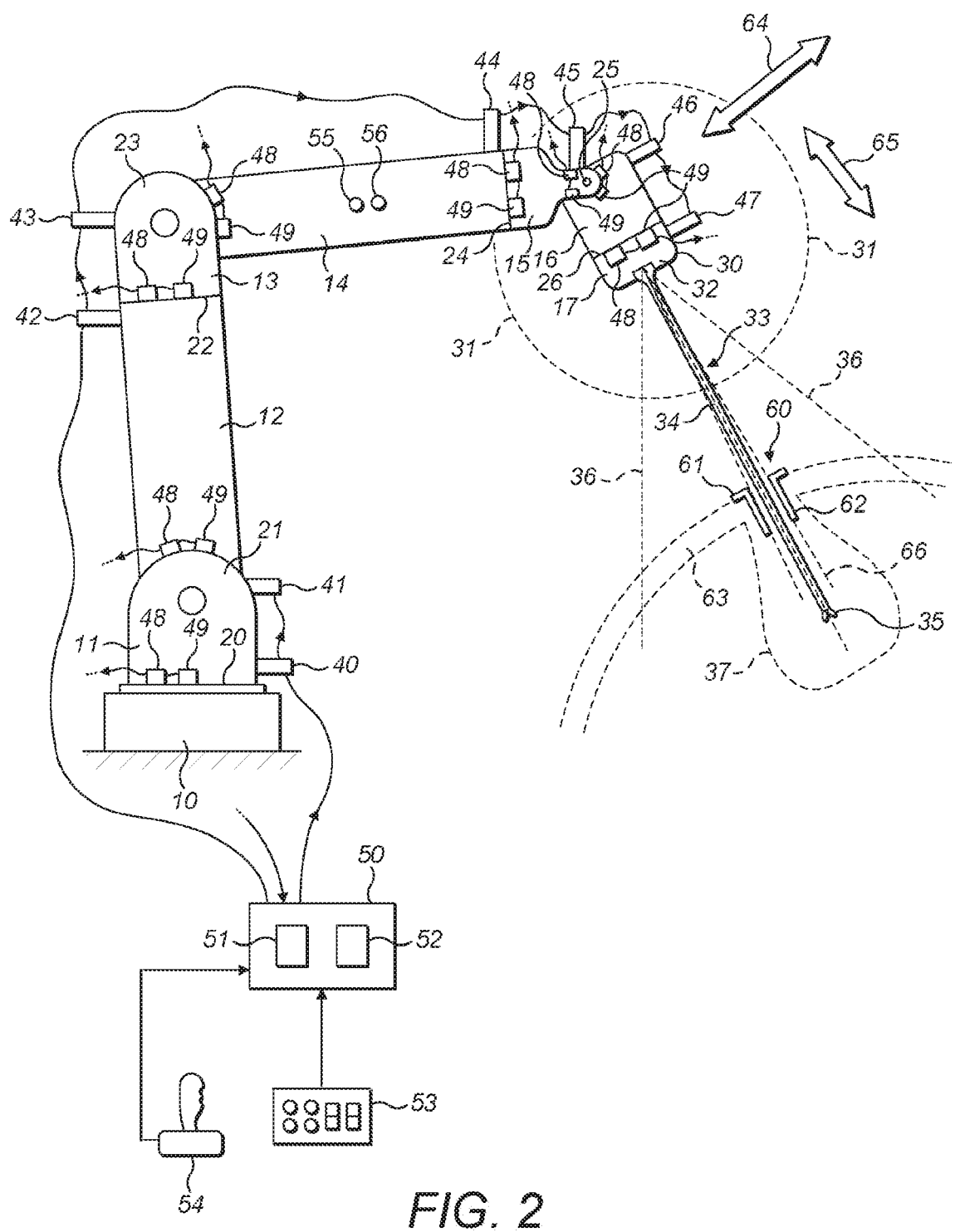
FIG. 2 illustrates a surgical robot.

FIG. 2 shows an example of a surgical robot. The robot comprises a base 10 which is fixed in place when a surgical procedure is being performed. The robot has a series of rigid arm members 11, 12, 13, 14, 15, 16, 17. The proximal arm member 11 is joined to the base 10 by a first revolute joint 20. Each other arm member in the series is joined to the preceding arm member by a respective joint 21, 22, 23, 24, 25, 26. Joints 21, 22, 23, 24 and 26 are revolute joints. Joint 25 is composed of two revolute joints whose axes are orthogonal to each other, as in a Hooke's or universal joint. The arm could be jointed differently from the arm of FIG. 2. For example, joint 23 could be omitted and/or joint 25 could permit rotation about a single axis. The arm could include joints that permit motion other than rotation between respective sides of the joint, for example a joint by which a tool attachment can slide linearly with respect to more proximal parts of the arm.

The joints are configured so that they provide the arm with flexibility allowing the distal end 30 of the robot arm to be moved to an arbitrary point in a three-dimensional working volume illustrated generally at 31. One way to achieve that is for the joints to have the arrangement illustrated in FIG. 2. There, the arm comprises the following joints:

a most distal joint 20 having a substantially vertical rotation axis, a succeeding joint 21 having a rotation axis transverse to the axis of joint 20, a succeeding joint 22 having a rotation axis transverse to the axis of joint 21 and extending generally between joint 21 and joint 23, a succeeding joint 23 having a rotation axis transverse to the axis of joint 22, a succeeding joint 24 having a rotation axis transverse to the axis of joint 23 and extending generally between joint 23 and joint 24, a succeeding joint 24 having a rotation axis transverse to the axis of joint 23, a succeeding joint 25 having two mutually transverse rotation axes, one of which is transverse to the axis of joint 24, and a succeeding joint 26 having a rotation axis transverse to the other of the axes of joint 25.

Other combinations and configurations of joints could achieve a similar range of motion, at least within the zone 31. There could be more or fewer rigid arm members.

The distal end of the robot arm has an attachment structure 32 by means of which a surgical tool 33 can be releasably attached to the distal end of the arm. The surgical tool has a linear rigid shaft 34 and a working tip 35 at the distal end of the shaft. The working tip comprises a device for engaging in a medical procedure, for example a cutting, grasping or imaging device. There could be additional parts of the arm extending beyond the location where the tool is attached. The tool and/or the attachment structure 32 may be configured so that the tool extends linearly parallel with the rotation axis of the terminal joint 26 of the arm. In this example the tool extends along an axis coincident with the rotation axis of joint 26.

Joints 24, 25 of the robot are configured so that with the distal end of the arm held at an arbitrary location in the working volume 31 the surgical tool 33 can be directed in an arbitrary direction within a cone. Such a cone is illustrated generally at 36. One way to achieve that is for the terminal part of the arm to comprise the pair of joints 24, 25 whose axes are mutually arranged as described above. Other mechanisms can achieve a similar result. For example, joint 26 could influence the attitude of the tool if the tool extends out of parallel with the axis of joint 26.

Joints 21, 23, 24 and 25 of the robot are configured so as to enable the tool to be moved parallel to the rotation axis of the terminal joint 26 of the arm in the direction generally indicated by 65, thereby enabling the tool to be inserted through the port into the patient and to be extracted from the patient through the port.

The arm comprises a series of motors 40, 41, 42, 43, 44, 45, 46, 47. With the exception of the compound joint 25, which is served by two motors, each motor is arranged to drive rotation about a respective joint of the arm. The motors are controlled by a control unit 50. The control unit comprises a processor 51 and a memory 52. The memory stores, in a non-transient way, software code that can be executed by the processor to cause the processor to control the motors 40-47 in the manner described herein.

The arm also comprises a series of sensors 48, 49. Conveniently these sensors comprise, for each joint, a position sensor 48 for sensing the positional state of the joint and a force sensor 49 for sensing applied torque about the joint's rotation axis. Compound joint 25 has two pairs of sensors. One or both of the position and torque sensors for a joint may be integrated with the motor for that joint. The outputs of the sensors are passed to the control unit where they form inputs for the processor 51. In addition, the processor receives inputs from a control panel 53, which allows the operating state of the arm to be selected, and from a three-dimensional controller 54, which allows an operator to signal to the control panel the three-dimensional movements required from the arm, e.g. when an operation is being performed.

The motion of the arm can be controlled in several modes. In a first, driven mode the configuration of the arm is set in dependence on the inputs received from the three-dimensional controller 54. In this mode the operator uses the three-dimensional controller to signal a desired position of the tool tip 35 and/or of the end 30 of the arm. The processor 51 determines a configuration of the joints of the arm that will result in the tool tip and/or the arm end being placed in that position. There may be multiple configurations of the arm that will result in the tool tip and/or the arm end being placed in the desired position. The processor may select between those configurations based on an algorithm that seeks to avoid collisions between the arm and other objects known to the processor to be near the arm, or that seeks to minimise the amount of movement of the joints to reach the new configuration. Once the processor has selected a new configuration it signals the joints 20-26 to adopt the states required to bring the arm into that configuration. In this way, in the driven mode the operator can signal the arm end and/or the tool tip to move to a desired location.

In a second, compliant mode the processor controls the arm to maintain a position in which it is placed by means of force applied directly to the arm. To achieve this the processor receives inputs from the position and force sensors 48, 49. From the position sensors the processor knows the current configuration of the arm. The memory 52 stores for each element of the arm, and the tool, its mass, the distance of its centre of mass from the preceding joint of the arm and the relationship between the centre of mass and the positional output of the joint sensor for the preceding joint. Using that information the processor models the effect of gravity on the elements of the arm for the current configuration of the arm and estimates a torque due to gravity on each joint of the arm. The processor then drives the motor of each joint to apply a torque that will exactly oppose the calculated gravitational torque. With this control strategy an operator can directly push or pull any part of the arm to a desired position, and the part will stay in that position notwithstanding the effect of gravity on it and on any parts depending from it. A force on the arm may result in a torque about multiple joints. The controller can be programmed to decide to prioritise certain ones of the joints for neutralising the torque. In the compliant mode some of the joints will experience no gravitational torque. The motors for those joints may be de-energised. More typically, each motor may be controlled in response to the torque measured about the respective joint. When the measured torque at a joint is adjusted for gravity any remaining torque represents a torque applied by a force due to a push on the arm or the tool. In response to that torque the controller may control the respective motor to move the joint in a direction so as to reduce the measured torque, and at a rate dependent on the magnitude of the measured torque, so that the arm provides the sensation of moving freely but with some resistance in response to applied force.

In a third, selectively compliant mode, the processor controls the arm to maintain a position in which it is placed by means of force applied directly to the arm as described with respect to the second, compliant mode. However, the processor controls the arm so as to only enable certain reconfigurations of the arm under the external forces. For these permitted reconfigurations, the joints move under the external forces applied as described in the second, compliant mode. For the remaining non-permitted reconfigurations, the processor controls the arm to resist the application of external forces. This may be implemented by the processor not signaling the motor to drive the joint. In this way, the compliance is selective.

FIG. 2 shows a surgical port 60 inserted in the abdominal wall 63 of a patient. The port comprises an outer plate 61, which extends radially outwardly of an incision through the abdominal wall to resist the port being pushed too far into the abdominal cavity, and guide tube 62 which extends inwardly of the plate 61. A passageway extends through the port from the plate to the inner end of the tube. When the tool 33 is in place for performing a procedure on the patient the shaft 34 of the tool is inserted through the passageway into the abdominal cavity, as illustrated in FIG. 2.

Conveniently there is/are one or more joints near the terminal end of the arm that permit the tool to be rotated about one or more axes transverse to its main direction of elongation.

The present robot is capable of calculating the location of the port, and particularly the port's natural centre of rotation, by means of manipulation of the robot arm when the robot is in compliant mode. First, the patient is prepared for surgery by inserting the port into the appropriate location in the patient's body (e.g. the abdominal wall), and the patient is positioned in the operating theatre at a fixed location within reach of the robot. Then, with the robot in compliant mode an operator can grasp one or both of the robot arm and the tool 33 and push them into a configuration such that the longitudinal axis of the shaft 34 of the tool is aligned with the passageway in the port. Then the operator can push on the robot arm and/or the tool so that the tool moves parallel to its longitudinal axis and passes into the passageway in the port. At this stage the tool can conveniently be inserted only partially into the port, so that the tip 35 of the tool is still within the passageway 62 of the port.

Now, with the tool or instrument 33 located in the passageway 62 of the port the operator can move the distal end 30 of the robot arm in directions generally transverse to the longitudinal axis 34 of the tool shaft, e.g. as indicated generally at 64. This motion will cause the port to exert a lateral force on the tool shaft where it passes through the port, with the result that the tool will apply a torque to the joints of the arm—in this case joints 24 and 25—whose axes are transverse to the tool shaft axis 34. Since the robot is operating in compliant mode that torque will be accommodated by motion about the joints 24, 25. As the operator moves the distal end of the robot arm laterally the controller 50 receives inputs indicating the position of the joints. That information allows the controller to estimate: (a) the position of the distal end of the robot relative to the base and (b) the vector of the tool shaft relative to the distal end of the robot. Since the tool shaft passes through the passageway of the port, the passageway of the port must lie along that vector. As the distal end of the robot arm is moved, the controller can calculate multiple pairs of distal end positions and tool shaft vectors. Those vectors, will all converge, from their respective distal end position, on the location of the passageway of the port. By collecting a series of those data pairs and then solving for the mean location where the tool shaft vectors converge the robot controller can estimate the location of the port relative to the base. The processor 51 executes code stored in memory 52 to estimate the location of the port as the location where the tool shaft vectors converge. Once the location of the port has been estimated, the controller stores the estimated location in memory, for example memory 52, and exits the compliant calibration mode.

To assist the controller 50 to estimate the port position the controller has knowledge of the relationship between the attitude of the terminal member 17 of the robot arm and the direction of the longitudinal axis of the tool shaft 34. That relationship may be constant independent of the tool, by virtue of the interface 32 between the arm and the tool being standardised. Alternatively, different tools may extend from the terminal member at different angles, in which case the operator may inform the controller of the type of tool fitted to the robot arm, or the controller may automatically detect the type of tool and configure its port detection algorithm in dependence on information stored in memory 52 regarding the relationship between the tool and the attachment. Alternatively, the controller may detect the relationship between the attitude of the terminal member of the robot arm and the direction of the tool shaft through the motion of the joints (e.g. joints 24 and 25) as the terminal member of the robot arm is agitated by the operator during the calibration process. Conveniently the tool shaft is straight and extends in a known direction from the end member 32 of the robot arm.

In the following example, a retraction mode is engaged prior to removing a tool from a patient. The retraction mode may be selected by an operator on the control panel 53. Alternatively, the retraction mode may be selected by user input 55 (this may be, for example, a push button) on the arm. Similarly, the other modes described above may be selected either solely by the control panel 53, solely by the user input 55, or by either one of the control panel 53 and user input 55. In the retraction mode for tool retraction, the processor 51 controls the motors to reconfigure the arm so as to cause the tool to be retracted from the port along the longitudinal axis 34 of the tool. As the tool is being withdrawn along the longitudinal axis 34 of the tool, the processor 51 controls the motors to reconfigure the arm so as to agitate the tool transverse to the longitudinal axis of the tool. This jiggling reduces the static friction between the port and the tool, thereby reducing the likelihood of the port pulling out of the patient as the tool is withdrawn from the patient.

Figure 3:
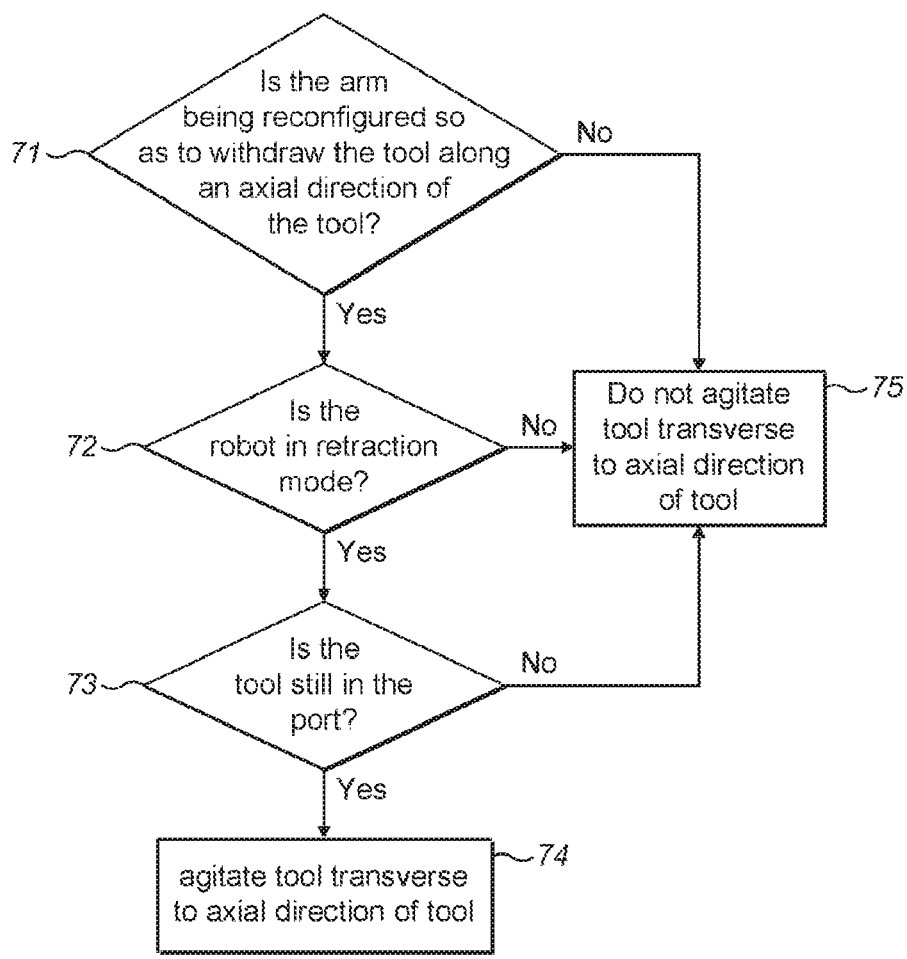
FIG. 3 illustrates a method of determining whether to agitate a tool transverse to the longitudinal axis of the tool.

The flowchart of FIG. 3 illustrates a decision process that the processor 51 may follow in order to determine whether to agitate the tool transverse to the longitudinal axis 34 of the tool. At step 71, the processor determines if the arm is being reconfigured so as to cause the tool to be moved along the longitudinal axis 34 of the tool away from the body. The following describes an exemplary way that step 71 may be implemented. From the position sensors 48, 49, the processor knows the current configuration of the arm. Thus, it knows the location of the attachment structure 32. The processor knows the most recently calculated location of the port 60 which is stored in memory, using the methods described herein. The processor may receive sensor input, from which it can determine the movement of the arm, and hence the movement of the attachment structure 32. It can thus determine if the attachment structure 32, and hence the tool 33, is moving away from the body in the direction of a straight line joining the port and the attachment structure 32. If the processor determines that the tool is not being moved along the longitudinal axis 34 of the tool away from the body, then the processor determines not to agitate the tool transverse to the longitudinal axis 34 of the tool at step 75. If the processor determines that the tool is being moved along the longitudinal axis 34 of the tool, then the processor moves to step 72. Although FIG. 2 illustrates sensors 48, 49 on the robot arm, sensors may in addition be located on the tool itself. Sensor input from the tool sensors may be fed back to the control unit 50 which uses that sensor input in the same manner as the sensor input from the arm sensors.

At step 72, the processor determines if the robot is in the retraction mode. This mode may have been selected from the control panel 53 or from user input 55 as described above. There are various reasons why the tool may be being retracted from the body. For example, the operator may be manipulating the tool inside the body in such a way that the shaft of the tool moves in and out of the port, for example this may happen during a suturing process. Thus, the processor only determines to agitate the tool transverse to the longitudinal axis 34 of the tool if the robot has first been placed in the retraction mode. If the robot is not in the retraction mode, then the processor determines not to agitate the tool transverse to the longitudinal axis 34 of the tool at step 75. If the processor determines that the tool is in the retraction mode, then the processor moves to step 73.

At step 73, the processor determines if the tool is still in the port. The following describes an exemplary way that step 73 may be implemented. The processor retrieves the most recently stored port location from memory, and also the location of the attachment structure 32. The memory 52 stores the length of the tool attached to the attachment structure 32. From this information, the processor determines if the tool intersects the port. The tool is determined to intersect the port if (i) the attachment structure 32 and the port 60 are aligned along the direction that a tool is attached to the attachment structure 32, and (ii) the distance between the attachment structure and the port is shorter than the length of the tool. If the tool is determined to intersect the port, then the tool is still in the port. In this case, the processor determines to agitate the tool transverse to the longitudinal axis 34 of the tool at step 74. If the tool is not determined to intersect the port, then the tool is determined to not still be in the port, in which case the processor determines to not agitate the tool transverse to the longitudinal axis 34 of the tool at step 75.

At step 74, the control unit 50, by means of the software stored in memory 52, selects a series of configurations of the arm which cause the attached tool to be agitated in a direction transverse to the longitudinal axis 34 of the tool. The control unit signals the motors of the joints of the arms to move so as to cause the agitation.

The steps of FIG. 3 could be implemented in a different order. The key feature of this exemplary implementation is that the tool is only agitated transverse to the longitudinal axis 34 of the tool if: (i) the arm is being reconfigured so as to withdraw the tool from the port along the longitudinal axis 34 of the tool, (ii) the robot is in the retraction mode, and (iii) the tool is still in the port.

The agitation to the tool may be implemented in any suitable way. For example, the control unit 50 may instruct the motor 47 to drive the joint 26 to rotate about its rotation axis. This causes the attachment structure 32, and hence the tool 33, to spin about the rotation axis of joint 26 which is also the longitudinal axis 34 of the tool 33. The control unit may periodically instruct the motor 47 to change the direction that it is driving the joint 26, thereby causing the direction of spin of tool 33 to change periodically. In other words, causing the tool 33 to twist back and forth about its longitudinal axis 34.

Instead, or in addition to the example above, the control unit 50 may cause the agitation of the tool by controlling the angular attitude of the attachment structure 32 relative to the base to be varied. This may be implemented, for example, by driving one or both of joints 24 and 25 about their axes. This causes the tool 33 to move in an arc centred on where the tool is attached to the attachment structure. This rocking is implemented with a low amplitude, so that the movement in the plane transverse to the longitudinal axis 34 of the tool is sufficient to reduce the static friction between the tool and the port but not so great as to exert excess force on the port which may cause damage to the skin incision area. For example, the movement may be constrained to a narrow cone 66.

In an alternative example, the attachment structure may be attached to the remainder of the arm via a joint which enables the attachment structure, and hence the tool, to be linearly displaced such that the longitudinal axis 34 of the arm member 16 is offset from the longitudinal axis 34 of the tool 33. For example, the attachment structure may be attached to the arm member 16 via a rail which enables the attachment structure to shift relative to the arm member 16 in the plane that is transverse to the longitudinal direction of the arm member 16. In this example, the control unit 50 may cause the agitation of the tool by controlling the joint between the arm member 16 and the attachment structure to shift the attachment structure, and hence the tool, from side to side relative to the arm member 16.

The control unit 50 may control the motors to drive the joints so as to agitate the tool transverse to the longitudinal axis 34 of the tool as a function of the retraction of the tool along the longitudinal axis 34 of the tool. The faster the tool is withdrawn through the port, the faster the agitation. Thus, the withdrawal of the tool has a screw-like effect. If the withdrawal stops whilst the tool is still in the port, then suitably, the agitation stops. Once the tool has been fully withdrawn from the port, the agitation stops.

The control unit controls the motors to reconfigure the arm so as to cause the tool to be retracted from the port along the longitudinal axis 34 of the tool. The control unit may take this action in response to receiving input from the operator via the control panel 53 or the 3D controller 54.

Alternatively, the control unit may take this action whilst in a selectively compliant mode and in response to detecting an external force applied to the arm along the longitudinal axis 34 of the tool away from the port. In this selectively compliant mode, the processor 51 controls the motors so as to permit the arm to be reconfigured by the action of an external force applied to the arm along the longitudinal axis 34 of the tool away from the direction of the port. In other words, an external force applied to the arm parallel with the shaft of the tool in a direction opposing the working tip of the tool, so as to cause the tool to be extracted from the patient. On detecting external force applied in this direction, the processor 51 responds by signaling the motors of the appropriate joints to drive the joints to move in the direction that the external force is applied. The force of gravity on each joint is opposed as described above with respect to the compliant mode. On detecting that the external force applied along the longitudinal axis 34 of the tool away from the direction of the port has ceased, the processor 51 responds by controlling the motors to stop driving the joints to move the tool in the direction of the longitudinal axis 34 of the tool away from the port. The processor continues to drive the joints to oppose the force of gravity on each port. The extraction of the tool out of the port thereby stops on detecting that the external force is no longer being applied in the direction of the longitudinal axis of the tool away from the port, and the robot arm and hence the tool remain in the position that they were moved to notwithstanding the effect of gravity. In this way, an operator can manually push the robot arm or the tool in a direction away from the port, and the robot arm responds by moving in that direction until the operator stops pushing the robot arm or tool at which point the robot arm maintains the position that it had reached. Thus, the arm provides the sensation to the operator of moving freely under his push to withdraw the tool from the port.

In this selectively compliant mode for tool retraction, external force applied in a direction transverse to the longitudinal axis 34 of the tool is not permitted. On detecting external force applied in such a direction, the processor 51 does not signal the motors to drive the joints. The external force applied in the direction is thereby resisted. Suitably, in this selectively compliant mode for tool retraction, external force applied along the longitudinal axis 34 of the tool towards the direction of the port is not permitted. On detecting external force applied along the longitudinal axis 34 of the tool towards the body, the processor 51 does not signal the motors to drive the joints. The external force applied in this direction is thereby resisted. The operator may apply the external force directly to the arm by manipulating the distal end 30 of the robot arm. Alternatively, the operator may apply the external force indirectly to the arm by directly contacting the tool to pull it out of the port 60.

The processor detects that an external force has been applied to the arm by means of force sensors attached to the robot arm. Alternatively, or in addition, force sensors may be attached to the tool 33. The sensors provide sensor input to the control unit 50. The processor uses this sensor input to determine if an external force has been applied to the arm or the tool, and hence to determine to respond by signaling the appropriate motors to drive the appropriate joints to comply with the applied external force if it is along the longitudinal axis of the tool away from the port.

The principles described above are applicable to other types of surgical robot than the one shown in FIG. 2. For example, the base of the robot could be floor-mounted, ceiling-mounted or mounted to a bed, trolley or table. The joints and members of the robot arm could be provided in any suitable way. The terminal element of the robot could be provided with a sliding rail by means of which the tool can be inserted through the port. The robot could be for purposes other than surgery. For example, the port could be an inspection port in a manufactured article such as a car engine and the robot could control a viewing tool for viewing inside the engine.

The device provided on the tool tip could be for any appropriate surgical or other procedure, for example cutting, holding, viewing, illuminating, irradiating or joining. Suitably, the shaft of the tool is straight, as is the passage in the port. Alternatively, the tool shaft and the port passage could be curved with a common radius.

The three-dimensional controller 54 could be remote from the robot. The controller 50 could operate the robot arm under programmatic control.

The position sensors could, for example, be potentiometers, optical position encoders, ultrasonic or radio distance sensors. The force sensors could, for example, be a resistance-based strain gauge, a piezoelectric strain gauge or a semiconductor strain gauge. The drivers for driving the joints of the robot to move could be rotary or linear motors, or means other than motors: for example hydraulic or pneumatic rams.

If the arm were entirely flexible then the force sensors could be omitted. However, this would make it more difficult for the operator to manipulate the arm without the tool imposing excessive load on the patient.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robot comprising:
  a base;
  a flexible arm extending from the base and having:
    a plurality of joints whereby a configuration of the arm can be altered,
    a plurality of drivers arranged to drive the joints to move, and
    an attachment structure configured to attach a tool, which is separate and distinct from the arm, to the arm; and
  a control unit, comprising a processor and a memory, configured to control the drivers in the arm and operable in a retraction mode in which, whilst the tool is attached to the attachment structure and captive in a port, the control unit:
    (i) controls the drivers in the arm to reconfigure the arm so as to cause the tool to be retracted from the port along a longitudinal axis of the tool; and
    (ii) on retracting the tool from the port along the longitudinal axis of the tool, controls the drivers in the arm to reconfigure the arm so as to agitate the tool transverse to the longitudinal axis of the tool.

2. The robot as claimed in claim 1, wherein the control unit is configured to control the drivers to agitate the tool by causing the attachment structure to rotate about the longitudinal axis of the tool.

3. The robot as claimed in claim 1, wherein the control unit is configured to control the drivers to agitate the tool by causing an angular attitude of the attachment structure relative to the base to be varied.

4. The robot as claimed in claim 1, wherein the control unit is configured to control the drivers to agitate the tool transverse to the longitudinal axis of the tool as a function of retracting the tool along the longitudinal axis of the tool.

5. The robot as claimed in claim 1, further comprising the tool attached to the attachment structure, the tool being a surgical tool.

6. The robot as claimed in claim 1, wherein the control unit is configured to:
  receive inputs from sensors, and
  on receiving sensor input indicating that the arm has been reconfigured so as to cause the tool to be retracted from the port along the longitudinal axis of the tool, controlling the drivers to reconfigure the arm so as to agitate the tool transverse to the longitudinal axis of the tool.

7. The robot as claimed in claim 1, wherein the arm comprises a plurality of sensors configured to sense forces applied about the joints, and the control unit is configured to, in the retraction mode, control the drivers in dependence on outputs of the sensors.

8. The robot as claimed in claim 5, wherein the tool comprises a plurality of sensors configured to sense forces applied to the tool, and the control unit is configured to, in the retraction mode, control the drivers in dependence on outputs of the sensors.

9. The robot as claimed in claim 1, wherein the control unit is configured to control the drivers to permit the arm to be reconfigured by action of an external force applied to the arm so as to cause the tool to be retracted from the port along the longitudinal axis of the tool.

10. The robot as claimed in claim 1, wherein in the retraction mode, the control unit is configured to control the drivers to prevent the arm from being reconfigured by action of an external force applied to the arm so as to cause the tool to move transverse to the longitudinal axis of the tool.

11. The robot as claimed in claim 1, wherein in the retraction mode, the control unit is configured to control the drivers to prevent the arm from being reconfigured by action of an external force applied to the arm so as to cause the tool to be further inserted into the port along the longitudinal axis of the tool.

12. The robot as claimed in claim 1, wherein the control unit is configured to, in the retraction mode, control the drivers so as to resist action of gravity and thereby cause the arm to maintain a configuration imposed by an external force independently of the action of gravity.

13. The robot as claimed in claim 1, wherein the control unit is configured to, in the retraction mode, control the drivers so as to present a limited resistance to reconfiguration under an external force independently of action of gravity.

14. The robot as claimed in claim 1, wherein the control unit is configured to initiate operation in the retraction mode in response to receiving input from an operator via at least one of a control panel, a 3D controller, or user input on the arm.

15. The robot as claimed in claim 1, wherein the control unit is configured to control the drivers to reconfigure the arm so as to cause the tool to be retracted from the port along the longitudinal axis of the tool in response to receiving a control input from an operator via at least one of a control panel, a 3D controller, or user input on the arm.

16. The robot as claimed in claim 1, wherein the control unit is operable in a driven mode in which, when the tool is attached to the attachment structure, the control unit receives a demand signal indicating a desired location of a part of the tool, calculates a configuration of the arm in which the part of the tool will be at the desired location and the tool intersects the location of the port, and controls the drivers so the arm adopts the calculated configuration.

17. The robot as claimed in claim 1, wherein the memory is configured to store non-transiently a set of instructions executable by the processor to implement the mode.

18. The robot as claimed in claim 1, wherein the robot is a surgical robot.

19. A method of controlling a robot, the robot comprising a base, a flexible arm extending from the base and having a plurality of joints whereby a configuration of the arm can be altered, a plurality of drivers arranged to drive the joints to move, and an attachment structure configured to attach a tool, which is separate and distinct from the arm, to the arm, the method comprising, whilst the tool is attached to the attachment structure and captive in a port:

controlling the drivers in the arm so as to reconfigure the arm so as to cause the tool to be retracted from the port along a longitudinal axis of the tool; and on retracting the tool from the port along the longitudinal axis of the tool, controlling the drivers in the arm to reconfigure the arm so as to agitate the tool transverse to the longitudinal axis of the tool.

20. A robot comprising:

a base;

an arm coupled to and extending from the base, the arm comprising an attachment structure to attach a tool, which is separate and distinct from the arm, to the arm;

a plurality of joints; and a plurality of drivers coupled to the plurality of joints to drive movement of the plurality of joints; and a control unit, comprising a processor and a memory, coupled to the plurality of drivers in the arm and configured to control the plurality of drivers in the arm to agitate the tool transverse to a longitudinal axis of the tool while retracting the tool from a port.

\* \* \* \* \*